United States Patent
Schneider et al.

(10) Patent No.: US 10,124,547 B2
(45) Date of Patent: Nov. 13, 2018

(54) METHOD OF IDENTIFYING AND/OR TRACKING DEFORMATION OF A TURBINE ENGINE PART

(71) Applicant: SAFRAN AIRCRAFTS ENGINES, Paris (FR)

(72) Inventors: Julien Schneider, Moissy Cramayel (FR); Ludovic Edmond Camille Molliex, Moissy Cramayel (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 503 days.

(21) Appl. No.: 14/431,517

(22) PCT Filed: Sep. 26, 2013

(86) PCT No.: PCT/FR2013/052281
§ 371 (c)(1),
(2) Date: Mar. 26, 2015

(87) PCT Pub. No.: WO2014/049283
PCT Pub. Date: Apr. 3, 2014

(65) Prior Publication Data
US 2015/0239183 A1    Aug. 27, 2015

(30) Foreign Application Priority Data
Sep. 28, 2012    (FR) .................... 12 59237

(51) Int. Cl.
*B29C 70/48*    (2006.01)
*G01N 23/046*    (2018.01)
(Continued)

(52) U.S. Cl.
CPC .............. *B29C 70/88* (2013.01); *B29C 70/62* (2013.01); *B29C 70/882* (2013.01);
(Continued)

(58) Field of Classification Search
CPC ............ B29C 47/1081; B29C 45/1816; B29C 2045/184; B29C 2045/185; B29C 70/683
See application file for complete search history.

(56) References Cited

U.S. PATENT DOCUMENTS 5,327,081 A    7/1994    Rudd et al.
5,423,222 A    6/1995    Rudd et al.
(Continued)

FOREIGN PATENT DOCUMENTS

| EP | 0 503 940 A2 | 9/1992 |
| EP | 0 905 509 A1 | 3/1999 |
| FR | 2 971 970 A1 | 8/2012 |

OTHER PUBLICATIONS

Amenabar et al., "Comparison and analysis of non-destructive testing techniques suitable for delamination inspection in wind turbine blades," Composites: Part B, vol. 42, 2011.*
(Continued)

*Primary Examiner* — Jacob T Minskey
*Assistant Examiner* — Baileigh Kate Darnell
(74) *Attorney, Agent, or Firm* — Oblon, McClelland, Maier & Neustadt, L.L.P.

(57) ABSTRACT

A method of identifying and/or tracking deformation of a mechanical part made of composite material for a turbine engine, in which the part includes a preform of fiber material and a resin, is provided. The method includes incorporating metal particles in the preform or the resin during fabrication of the part, and subjecting the mechanical part to two X-ray inspections on two different occasions so as to identify the part and/or so as to deduce deformation of its internal structure.

10 Claims, 2 Drawing Sheets

(51) Int. Cl.
*B29C 70/88* (2006.01)
*B29C 70/62* (2006.01)
*G01N 23/083* (2018.01)
*B29K 505/00* (2006.01)

(52) U.S. Cl.
CPC ......... *G01N 23/046* (2013.01); *G01N 23/083* (2013.01); *B29C 70/48* (2013.01); *B29K 2505/00* (2013.01); *G01N 2223/419* (2013.01); *G01N 2223/615* (2013.01); *G01N 2223/646* (2013.01)

(56) References Cited

U.S. PATENT DOCUMENTS

| 6,041,132 | A | 3/2000 | Isaacs et al. | |
| 6,623,543 | B1* | 9/2003 | Zeller | B01D 39/06 |
| | | | | 420/417 |
| 6,776,600 | B1* | 8/2004 | Zahoransky | B01F 5/0615 |
| | | | | 425/130 |
| 2008/0145647 | A1* | 6/2008 | Ganguli | B29C 70/025 |
| | | | | 428/328 |
| 2012/0025827 | A1 | 2/2012 | Tralshawala et al. | |

OTHER PUBLICATIONS

Germaneau et al., Comparison between X-ray micro-computed tomography and optical scanning tomography for full 3D strain measurement by digital volume correlation, NDT&E International, vol. 41, 2008.*

Jordan et al., "Microradiographic Strain Measurement Using Markers," Experimental Mechanics, vol. 34, Issue 2, pp. 155-165, Jun. 1994.*

International Search Report dated Dec. 3, 2013 in PCT/FR13/052281 Filed Sep. 26, 2013.

* cited by examiner

METHOD OF IDENTIFYING AND/OR TRACKING DEFORMATION OF A TURBINE ENGINE PART

BACKGROUND OF THE INVENTION

Field of the Invention

The present invention relates to a method of identifying and/or tracking deformation of a mechanical part for a turbine engine, such as an airplane turboprop or turbojet.

Description of the Related Art

At present, numerous non-destructive inspection techniques serve to track deformation of turbine engine parts in order to determine how their structure varies over time.

Nevertheless, those techniques, such as penetrant testing for example, are suitable for inspecting only the surfaces of parts, and they do not give information about internal deformation of a part. Thus, by way of example, after an incident such as an impact, or in the event of a maintenance operation, it is possible to determine whether or not cracks are present in the surface of the part, but it is not possible to determine the state of the internal structure of the part.

Furthermore, in order to keep track of mechanical parts, it is important to be able to distinguish parts from one another. In particular, when a non-destructive inspection method is applied to a series of similar parts such as blades or vanes for a fan or a compressor, for example, it must be possible to distinguish between the parts in order to enable each part to be individually traceable. At present, it is necessary to have recourse to external marking methods (writing identification numbers or sticking on labels) that enable the parts to be identified and distinguished from one another so long as their identification marks are not destroyed or do not become illegible.

It is known to use the X-ray tomography technique for obtaining information about the internal structure of a part. Nevertheless, that technique is not applicable to identifying and/or tracking deformation of turbine engine parts, in particular parts made of composite material.

BRIEF SUMMARY OF THE INVENTION

A particular object of the present invention is to provide a solution to the above-mentioned problems that is simple, effective, and inexpensive.

To this end, the invention provides a method of identifying and/or tracking deformation in a mechanical part made of composite material for a turbine engine, the part comprising a preform of fiber material together with resin, the method being characterized in that it consists in:
- incorporating metal particles in the preform and/or the resin while fabricating the part;
- subjecting the mechanical part to a first X-ray inspection so as to obtain first information about the positions of particles within the part; then
- subjecting the mechanical part to a second X-ray inspection on a later occasion so as to obtain second information about the positions of particles within the part; and
- identifying the part and/or deducing the deformation of its internal structure by comparing the first information about the positions of particles within the part as obtained with the first X-ray inspection and the second information as obtained with the second X-ray inspection.

In the method of the invention, the metal particles incorporated in the mechanical part form a three-dimensional pattern within the part that can be detected using X-rays because X-rays are attenuated by metal particles.

When the X-ray inspection operation consists in acquiring a single attenuation image through the part, information is obtained about the positions of the particles by viewing the positions of the particles in the attenuation image. By comparing two attenuation images as obtained by the first and second X-ray inspections, it is thus possible to identify a part compared with other parts, providing the particles are arranged uniquely in each part.

According to another characteristic of the invention, the first and second X-ray inspections consist in X-ray tomography inspections so as to obtain respective first and second three-dimensional measurements of the positions of metal particles within the part.

X-ray tomography gives access to the real positions in three dimensions of the metal particles within the part.

When the particles are arranged uniquely inside the part, this three-dimensional measurement makes it possible firstly to identify the mechanical part and secondly to obtain a three-dimensional representation of the internal structure of the part.

By carrying out another X-ray tomography inspection on a later occasion, another three-dimensional measurement is obtained of the positions of the metal particles, which can be compared with the first measurement in order to identify the part. Furthermore, comparing three-dimensional measurements makes it possible to visualize internal deformations of the part between the occasions on which the measurements were taken.

Advantageously, the first information is obtained from the mechanical part before any use is made thereof, thus making it possible to obtain an indication about the state of the internal structure of the part prior to any use, i.e. in its state free from deformation.

When performing inspection by X-ray tomography, the information that is obtained consists in a three-dimensional measurement of the positions of the metal particles within the part. It is thus possible to know accurately the state of the three-dimensional internal structure of the part prior to use.

In a first implementation of the method of the invention, at least some of the metal particles are introduced into a flow channel for a stream of resin having its downstream end leading into a mold housing the preform of fiber material.

Advantageously, the method comprises means for controlling the flow rate of metal particles in the stream of resin. In this way, it is possible to control the distribution of particles inside the preform progressively while the resin is being incorporated in the preform, thereby creating a desired three-dimensional arrangement of particles inside the part.

In a second implementation of the method of the invention, at least some of the metal particles are deposited on the preform before injecting the resin.

In comparison with the above-described method, this second method makes it possible to control more accurately the positions of particles on the part and to obtain a more accurate distribution of particles on the preform.

In practical manner, the particles may be deposited on the preform by means of a screen having a plurality of orifices of different diameters distributed in a predetermined pattern.

The predetermined pattern of the orifices contributes to distributing particles on the preform, thereby making it possible to create a single pattern of particles of given dimensions on the preform, enabling it to be identified by X-ray inspection.

Advantageously, the method consists in giving one or more predetermined orientations to the particles by applying a magnetic field. The use of a magnetic field is particularly advantageous when the particles are introduced into the mold by means of the stream of resin. Controlling the magnetic flux thus makes it possible to modify the viscosity and the speed of the stream of resin inside the mold, thereby modifying the distribution of particles in the preform.

The particles are preferably of density greater than the densities of the preform and of the resin, thereby enabling the metal particles to attenuate X-rays more strongly than the preform and the resin, so that the particles show up clearly.

The particles may be made of a metal material selected from titanium, nickel, aluminum, chromium, and iron.

The metal particles are advantageously spherical in shape with a diameter lying in the range about a few tens of micrometers to a few hundreds of micrometers, e.g. 20 micrometers (μm) to 300 μm. The particles preferably have a diameter lying in the range 20 μm to 50 μm, so that the particles have no impact on the mechanical strength of the blades or vanes.

In particular implementations of the invention, the composite material is a ceramic matrix material or an organic matrix material and the part is a turbine engine blade or vane.

BRIEF DESCRIPTION OF THE SEVERAL VIEWS OF THE DRAWINGS

Other advantages and characteristics of the invention appear on reading the following description made by way of non-limiting example and with reference to the accompanying drawings, in which.

Figure 1:
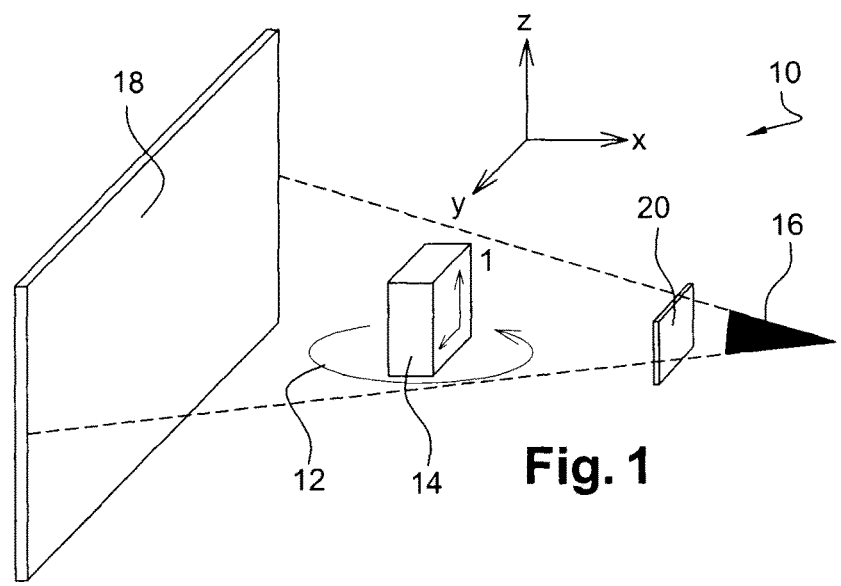
FIG. 1 is a diagrammatic perspective view of an X-ray tomography measuring device.

Reference is made initially to FIG. 1 which shows a device 10 for non-destructive inspection of a mechanical part by using X-ray tomography. The device 10 comprises a support 12 that is rotatable about an axis Z perpendicular to a plane XY and that has a mechanical part 14 for analysis mounted thereon. The part 14 is interposed between an X-ray source 16 emitting a beam of X-rays that pass through the part 14, and a plane detector 18 formed by a plurality of individual detectors. A filter 20 is interposed between the X-ray source 16 and the mechanical part 14 so as to prevent X-rays passing at energy levels that are unnecessary. The filter 20 is formed by a metal plate, e.g. made of copper, having thickness of the order of 0.1 millimeters. This type of device 10 is well known to the person skilled in the art and is not described in greater detail.

X-ray tomography consists in directing the X-ray beam through the part 14 and in using the detector 18 to acquire an image of the X-rays as attenuated on passing through the part 14. Thereafter, the movable support 12 is turned through a predetermined angle, and X-rays are acquired once more through the part 14. The above operation is repeated n times until the movable support 12 has performed a complete revolution through 360°. In a practical embodiment, a complete acquisition over 360° involves obtaining about 2000 images.

Thereafter, the attenuation images obtained at the various angular positions of the part 14 relative to the X-ray source 16 are transferred to a device for performing analysis, processing, and mathematical reconstruction.

According to the invention, the mechanical part for analyzing is made of composite material comprising a preform of fiber material having a resin injected therein.

The method of the invention consists in incorporating metal particles in the preform or in the resin while fabricating the part. Incorporating metal particles within the part serves to form density non-uniformities within the part, which give rise to attenuation non-uniformities of the X-rays that can be seen in the attenuation images recorded by the detectors for the various angular positions of the part. These metal particles thus form a three-dimensional microstructure that can be identified by X-ray tomography.

By applying a mathematical tomographic reconstruction procedure, known to the person skilled in the art, it is possible to use the attenuation images for the various angular positions of the support to obtain a three-dimensional measurement of the positions of the metal particles within the part.

The method of the invention consists in subjecting the part to non-destructive inspection by X-ray tomography on a first occasion and in obtaining a first three-dimensional measurement of the positions of the metal particles within the part. On a later occasion, a second X-ray tomography inspection is performed to obtain a second three-dimensional measurement of the positions of the particles.

Figure 2:
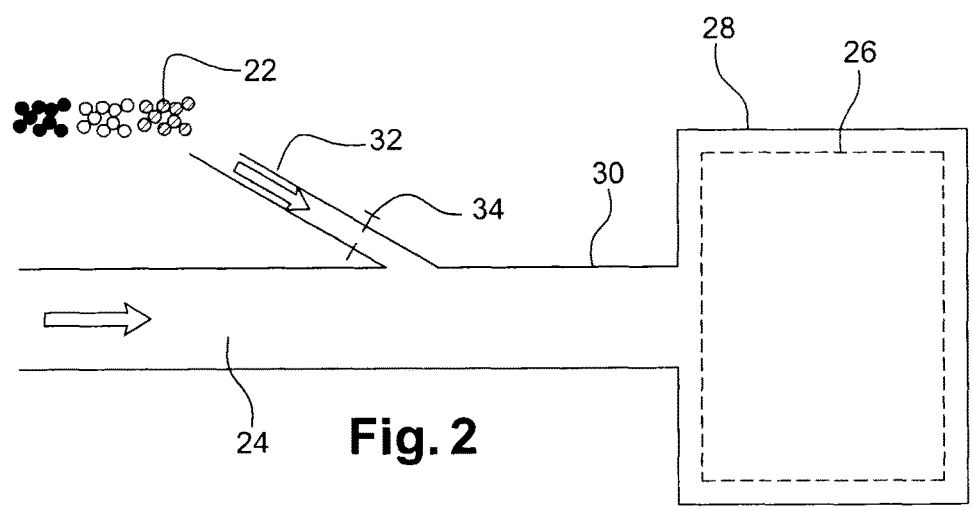
FIG. 2 is a diagram showing a first implementation of the method of the invention.
Figure 3:
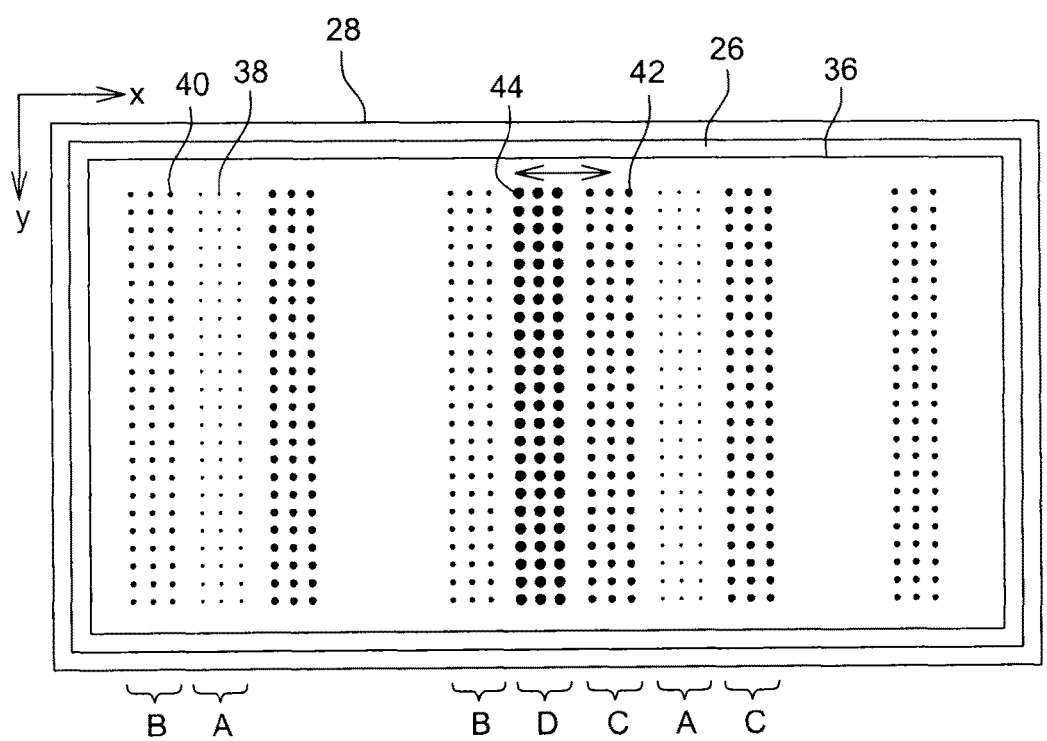
FIG. 3 is a diagram showing a second implementation of the method of the invention.

By comparing the first and second measurements, it is possible to identify the part and to measure internal deformations therein as can be seen more clearly with reference to FIGS. 2 and 3, which describe two particular implementations of the method.

In a first implementation of the method of the invention, as shown in FIG. 2, the metal particles 22 are incorporated in the stream of resin 24 and the resin-and-particle mixture is injected into the fiber perform 26.

For this purpose, the injection mold 28 housing the preform 26 and into which the resin 24 is injected is connected to the downstream end of a channel 30 along which the stream of resin 24 flows. The metal particles 22 are incorporated in the resin 24 via an auxiliary channel 32 in which the flow rate 34 of the particles 22 in the stream of resin 24 is controlled.

Thus, by controlling the flow rate of particles 22, it is possible to control the distribution of the particles 22 inside the preform 26 as injection of the mixture into the preform 26 progresses. It is thus possible to cause one part to present a first distribution of particles inside its preform and another part to present another distribution of particles that is different from the first distribution. As a result, the parts formed in this way have particle microstructures that are different. Tomographic inspection of the two parts makes it possible to obtain different three-dimensional measurements for the particles, thereby enabling the two parts to be distinguished even though both parts are of the same kind, such as two blades or vanes, for example.

The particle flow rate may either be constant throughout the injection of the resin 24 in order to have a substantially uniform distribution of particles within the preform 26, or else it may be varied during the injection of the resin 24 so as to have a distribution of particles 22 in a pattern that corresponds to the variation in the flow rate of the particles 22. When the flow rate is constant, it is possible to select a flow rate Q1 for one given part and a different flow rate Q2 for a second given part in order to distinguish them by X-ray tomography.

The particles 22 injected into the resin stream 24 may be made of materials that are identical or different and/or that have diameters that differ.

In a second implementation of the method of the invention, the particles 22 are incorporated in the preform by being deposited on its surface by means of a screen 36 prior to injecting the resin into the preform 26.

For this purpose, the preform is pre-positioned in its injection mold 28 and the screen 36 is positioned in a horizontal XY plane at some minimum distance that avoids any contact between the screen 36 and the preform 26. In practice, this distance is greater than 2 centimeters (cm). It is preferably also less than 50 cm.

The filter screen 36 has a plurality of orifices 38, 40, 42, 44 that are of different diameters and that are distributed in a predetermined pattern corresponding to the desired distribution of particles on the preform 26.

The screen 36 shown in FIG. 3 has a plurality of groups A, B, C, and D of rows of same-diameter orifices, these groups being spaced apart from one another along the direction X. Each group A, B, C, and D has three rows of orifices all of the same diameter. Certain groups A are formed with rows of orifices 38 of very small diameter, for example having a diameter lying in the range 20 μm to 50 μm. Other groups B are formed with rows of orifices 40 of small diameter, e.g. of diameter lying in the range 50 μm to 80 μm. Still other groups C are formed with rows of orifices 42 of medium diameter, e.g. lying in the range 80 μm to 150 μm. Finally, last group D is formed with rows of orifices 44 of large diameter, e.g. lying in the range 150 μm to 300 μm.

A support (not shown) may be arranged over the screen, which support includes partitions separating the various groups of orifices A, B, C, and D, each group co-operating with respective particle feed means so that the orifices in each group A, B, C, and D are fed with particles of a given diameter only.

The particles of different diameters may also be delivered simultaneously onto the entire surface of the screen so that the particles of very small diameter can pass through all of the orifices in the groups A, B, C, and D.

In other screen embodiments, the orifices may represent some other distribution and be in the form of rows of same-diameter orifices, which rows could be spaced apart in the direction X. In still other embodiments, the orifices could be aligned along lines that are curved instead of being straight. It can be understood that numerous screen patterns may be provided in order to obtain desired distributions of particles on preforms.

It can be understood that the distribution of the orifices and the way their diameters vary contribute to defining a unique microstructure of particles on any one preform that can be detected by X-ray tomography for identifying a given part.

By using a different screen for each part, it is possible to distinguish the parts from one another by performing X-ray tomography inspection.

It should be observed that it is also possible to distinguish the parts from one another while using only one screen, e.g. by varying the initial position of the screen over the preform and by varying the way it moves over the part.

The screen may be moved back and forth in translation over the preform through a distance lying in the range 0.5 cm to 5 cm, for example. The movement of the screen may be adapted as a function of the size of the part and of the desired positioning and covering of particles on the preform.

The particles deposited on the preform 26 may either be made of a single material or they may be made of different materials.

After particles have been incorporated in the preform 26 by means of the stream of resin or after being deposited by screening, the method of the invention may also include a step consisting in giving one or more predetermined orientations to the metal particles by applying a magnetic field.

In a practical implementation of the invention, the metal particles are selected from titanium, nickel, aluminum, chromium, and iron.

In a practical implementation of the invention, the particles may be of a diameter lying in the range about 20 μm to 300 μm.

In practice, the particles need to have a diameter d satisfying the following equation:

$$\frac{R}{10} < d < R$$

where: R is the resolution of the X-ray tomography device.

This equation is applicable for materials having density lying in the range 2 grams per cubic centimeter (g/cm$^3$) to 10 g/cm$^3$.

In general manner that is well known to the person skilled in the art, the detectability of particles by X-ray tomography is a function of the density and of the diameter of the particles.

In the invention, by incorporating metal particles in the fiber preform, it is possible to identify one particular mechanical part from among others by means of the three-dimensional internal microstructure formed by the metal particles. For a given part, by comparing the three-dimensional microstructure of the metal particles on different occasions, it is also possible to deduce therefrom the deformation of the internal structure of the part over time.

Numerous forms of particle microstructure may be obtained by using:
 particles of different densities, i.e. particles made of different materials; and/or
 particles of different diameters; and/or
 different distributions of particles within the part.

In another implementation of the invention, it is also possible to combine introducing particles into the preform as described with reference to FIG. 2 with incorporating metal particles in the preform using a screen as described with reference to FIG. 3.

In the particular circumstance in which the particles are arranged in a single manner, it is also possible to envisage acquiring X-rays transmitted through the part with the X-ray source and the detector being in a single position. Under such circumstances, an image is obtained of the attenuation of the X-rays transmitted through the part 14 that makes it possible to distinguish the part under analysis from another part having a different arrangement of particles.

It should be observed that using a single X-ray attenuation image can make it possible to access deformation of the internal structure of the part. Nevertheless, in order to obtain accurate information about internal deformation of the part, it is necessary to perform X-ray tomography inspection as described above so as to have three-dimensional measurements of the positions of the particles in the part.

The method of the invention may also be advantageous in the context of a machining operation for relieving residual stresses inside the material. For this purpose, the method of the invention may be applied by performing X-ray tomography inspection before the machining operation followed by second inspection after the machining operation on a part that includes a microstructure of metal particles, thus making it possible subsequently to evaluate the impact of stress relief on the internal structure of the part by comparing the three-dimensional measurements of the positions of the particles before and after machining.

The method of the invention is also advantageous for examining a part that has been subjected to a rise in temperature that could also lead to relieving residual stresses.

The invention claimed is:

1. A method of identifying and/or tracking deformation in a mechanical part made of composite material for a turbine engine, the part comprising a preform of fiber material together with resin, the method comprising:
   incorporating metal particles in at least one of the preform and the resin while fabricating the mechanical part;
   subjecting the mechanical part to a first X-ray inspection so as to obtain first information about positions of the metal particles within the mechanical part;
   subjecting the mechanical part to a second X-ray inspection on a later occasion so as to obtain second information about positions of the metal particles within the mechanical part; and
   at least one of identifying the part and deducing the deformation of an internal structure of the mechanical part by comparing the first information about the positions of the metal particles within the mechanical part as obtained respectively with the first X-ray inspection and the second information about the positions of the metal particles as obtained with the second X-ray inspection,
   wherein the metal particles incorporated in the mechanical part form a three-dimensional pattern within the mechanical part,
   wherein the first and second X-ray inspections include X-ray tomography inspections so as to obtain respective first and second three-dimensional measurements of the positions of metal particles within the mechanical part, and
   wherein a diameter of the metal particles is less than a resolution of an X-ray tomography device which performs the X-ray tomography inspections and greater than 10% of the resolution of the X-ray tomography device, the material used in the metal particles having a volumetric mass lying in a range of 2 $g/cm^3$ to 10 $g/cm^3$.

2. The method according to claim 1, wherein the first information is obtained from the mechanical part before any use is made thereof.

3. The method according to claim 1, wherein at least some of the metal particles are introduced into a flow channel for a stream of resin, a downstream end of the flow channel leading into a mold housing the preform of fiber material.

4. The method according to claim 3, further comprising controlling a flow rate of the metal particles in the stream of resin.

5. The method according to claim 1, further comprising depositing at least some of the metal particles on the preform prior to injecting the resin.

6. The method according to claim 5, wherein the metal particles are deposited on the preform by a screen having a plurality of orifices of different diameters distributed in a predetermined pattern.

7. The method according to claim 1, further comprising giving one or more predetermined orientations to the metal particles by applying a magnetic field.

8. The method according to claim 1, wherein the metal particles are of density greater than densities of the preform and of the resin.

9. The method according to claim 1, wherein the mechanical part is a turbine engine blade or vane.

10. The method according to claim 7, wherein a magnetic flux is controlled to modify a viscosity and a speed of a stream resin flowing inside a mold housing the preform of fiber material, thereby giving the one or more predetermined orientations to the metal particles.

* * * * *